(12) United States Patent
Kuliopulos

(10) Patent No.: US 9,878,054 B2
(45) Date of Patent: *Jan. 30, 2018

(54) POLYPEPTIDE AND LIPOPHILIC MOIETY CONJUGATE COMPOSITIONS, FORMULATIONS, AND USES RELATED THERETO

(71) Applicant: Tufts Medical Center, Inc., Boston, MA (US)

(72) Inventor: Athan Kuliopulos, Winchester, MA (US)

(73) Assignee: Tufts Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/403,187

(22) PCT Filed: May 17, 2013

(86) PCT No.: PCT/US2013/041512
§ 371 (c)(1),
(2) Date: Nov. 23, 2014

(87) PCT Pub. No.: WO2013/173676
PCT Pub. Date: Nov. 21, 2013

(65) Prior Publication Data
US 2015/0216990 A1    Aug. 6, 2015

Related U.S. Application Data

(60) Provisional application No. 61/648,789, filed on May 18, 2012.

(51) Int. Cl.
| | | |
|---|---|---|
| *A61K 38/08* | (2006.01) | |
| *A61K 47/26* | (2006.01) | |
| *A61K 47/48* | (2006.01) | |
| *A61K 9/00* | (2006.01) | |
| *A61K 9/107* | (2006.01) | |
| *A61K 9/19* | (2006.01) | |
| *A61K 38/17* | (2006.01) | |
| *A61K 45/06* | (2006.01) | |
| *C07K 14/705* | (2006.01) | |

(52) U.S. Cl.
CPC .......... *A61K 47/488* (2013.01); *A61K 9/0019* (2013.01); *A61K 9/1075* (2013.01); *A61K 9/19* (2013.01); *A61K 38/08* (2013.01); *A61K 38/177* (2013.01); *A61K 45/06* (2013.01); *A61K 47/26* (2013.01); *A61K 47/48038* (2013.01); *A61K 47/48046* (2013.01); *A61K 47/48238* (2013.01); *C07K 14/705* (2013.01)

(58) Field of Classification Search
None
See application file for complete search history.

(56) References Cited

U.S. PATENT DOCUMENTS

| | | | |
|---|---|---|---|
| 6,696,412 B1 * | 2/2004 | Kelleher | A61K 38/10 435/886 |
| 7,476,386 B1 * | 1/2009 | Gras-Masse | A61K 39/015 424/184.1 |
| 7,696,168 B2 * | 4/2010 | Kuliopulos | G01N 33/567 514/20.6 |
| 2006/0030578 A1 * | 2/2006 | Ahmad | A61K 31/4745 514/283 |

* cited by examiner

*Primary Examiner* — Marianne P Allen
(74) *Attorney, Agent, or Firm* — Milstein Zhang & Wu LLC; Duan Wu, Esq.

(57) ABSTRACT

In certain embodiments, this disclosure relates to pharmaceutical formulations for polypeptide and lipophilic moiety conjugates suitable for injection into humans and other animals and methods of preparation. In certain embodiments, the disclosure relates to a method of preparing the formulation comprising lyophilizing, solubilizing in ammonium acetate, filtering to create mono-disperse particles, re-lyophilizing, and solubilizing the micelles in a dextrose solution for injection.

2 Claims, 6 Drawing Sheets

POLYPEPTIDE AND LIPOPHILIC MOIETY CONJUGATE COMPOSITIONS, FORMULATIONS, AND USES RELATED THERETO

CROSS REFERENCE TO RELATED APPLICATIONS

This application claims priority to U.S. provisional application No. 61/648,789 filed May 18, 2012, hereby incorporated by reference in its entirety.

STATEMENT REGARDING FEDERALLY FUNDED RESEARCH

This invention was made with Government support under Grant No. RC2 HL101783 awarded by the National Institutes of Health. The government has certain rights in this invention.

BACKGROUND

Disruption of atherosclerotic plaques and formation of occlusive platelet thrombi remains a leading cause of morbidity and mortality in the United States. Antiplatelet therapies are used in preventing arterial thrombosis and myocardial infarction in high risk patients with acute coronary syndromes (ACS), atherothrombotic disease, and in patients who have undergone percutaneous coronary intervention (PCI). Current antiplatelet therapy for secondary prevention of vascular events mainly consists of oral administration of aspirin and thienopyridines. Patients with a higher risk of thrombosis while undergoing coronary interventions are also often treated with intravenous GP IIb/IIIa antagonists in addition to aspirin, thienopyridine, and heparin. Although dual antiplatelet therapy has been shown to attenuate ischemic event occurrence during ACS and PCI, drug response variability, the persistent occurrence of ischemic events, and the increased risk of bleeding events remain major concerns. Notably, approximately 10% of patients still suffer from recurrent ischemic events within one year of treatment. Thus, there is a need to identify improved therapeutic strategies.

Pepducin compounds are lipidated peptides that target specific intracellular loops of G-protein-coupled receptors (GPCRs) and are allosteric modulators of GPCR activity. The lipid moiety facilitates translocation across the plasma membrane where pepducin compounds modulate signaling of their cognate receptors. See Covic et al., PNAS, 2002, 99(2):643-64. The thrombin receptor, PAR1, is a GPCR that is a target for therapeutic intervention in conditions or diseases associated with undesirable platelet aggregation. See Chintala et al., J Pharmacol Sci. 2008, 108(4):433-438 and Leger et al., Circulation, 2006, 113(9):1244-1245. A pepducin compound, PZ-128 (also known as P1pal-7) has been reported. See WO/2010/118435. See also US Published Application 2007/0179090 and Wielders et al., J Thromb Haemost, 2007, 5(3):571-576.

SUMMARY

In certain embodiments, this disclosure relates to pharmaceutical formulations for polypeptide and lipophilic moiety conjugates suitable for injection into humans and other animals and methods of preparation. In certain embodiments, the disclosure relates to a method of preparing the formulation comprising lyophilizing, solubilizing in ammonium acetate, filtering to create mono-disperse particles, re-lyophilizing, and solubilizing the micelles in a dextrose solution for injection.

In certain embodiments, the disclosure relates to polypeptide and lipophilic moiety conjugate product forms produced by methods disclosed herein and therapeutic methods related thereto. In certain embodiments, the disclosure relates to compositions comprising micelle particles in substantially pure form comprising a polypeptide and lipophilic moiety conjugate containing nitrogen groups capable of forming carboxylic acid salts, e.g., PZ-128. In certain embodiments, the micelle forms acetic acid salts.

In certain embodiments, the polypeptide and lipophilic moiety conjugate is a PAR1, PAR2, PAR3, or PAR4 pepducin compound. In certain embodiments, the polypeptide is a fragment derived from PAR1, PAR2, PAR3, or PAR4, i1, i2, i3, i4 intracellular loops. In certain embodiments, the polypeptide is a fragment derived from a GPCR i1, i2, i3, i4 intracellular loops. In certain embodiments, the GPCR is a member of the Rhodopsin family. In the polypeptide and lipophilic moiety conjugate salts are palmitate-KKSRALF-$NH_2$ acetic acid salts.

In certain embodiments, the polypeptide and lipophilic moiety conjugate is palmitate-KKSRALF-$NH_2$. In certain embodiments, the micelle comprises a palmitate-KKSRALF-$NH_2$ acetic acid salt with approximately one, two, or three acetic acid counterions per polypeptide and lipophilic moiety conjugate. In certain embodiments, the micelle averages about one to five acetic acids or carboxylic acid groups in counter anions per palmitate-KKSRALF-$NH_2$ cation.

In certain embodiments, the disclosure relates to palmitate-KKSRALF-$NH_2$ salts wherein the counterion is selected from adipic acid, camphoric acid, carbonic acid, cinnamon acid, citric acid, fumaric acid, galactaric acid, gentisic acid, glucaric acid, glucoheptonic acid, D-gluconic acid, D-glucuronic acid, gluataric acid, alpha-oxo-glutaric acid, lactobionic acid, maleic acid, L-malic acid, malonic acid, pamoic acid, pyruvic acid, salicylic acid, sebacic acid, succinic acid, tartaric acid, or combinations thereof. In certain embodiments, the disclosure relates to palmitate-KKSRALF-$NH_2$ salts wherein the counterion is ascorbic acid. In certain embodiments, the salt may be in a composition optionally comprising sodium, ammonium, imidazole or combinations thereof.

In certain embodiments, the disclosure relates to pharmaceutical compositions comprising palmitate-KKSRALF-$NH_2$ salts in combination with mannitol, glucuronic acid, or combinations thereof.

In certain embodiments, the disclosure relates to pharmaceutical composition comprising micelle particles disclosed herein and a pharmaceutically acceptable excipient. In certain embodiments, the pharmaceutical composition is an aqueous solution comprising a saccharide or polysaccharide at about or less than 5% by weight. In certain embodiments, the pharmaceutically acceptable excipient is dextrose, sorbitol, or ethanol. In certain embodiments, the excipients create a buffered solution of a pH of about 7 or about in between, 5.0 and 9.0 pH, or about in between 5.5 and 8.5. In certain embodiments, the micelles are made by the process of freezing an aqueous solution comprising a polypeptide and lipophilic moiety conjugate and ammonium acetate providing ice, and placing the ice under a reduced pressure such that volatile substances are removed. In certain embodiments, the micelles the micelles are made by the process of freezing an aqueous solution comprising polypeptide and lipophilic moiety conjugates and sorbitol providing ice, and placing the ice under a reduced pressure such that volatile substances are removed. In certain embodiments, the micelles the micelles are made by the process of freezing an aqueous solution comprising polypeptide and lipophilic moiety conjugates and ethanol providing ice, and placing the ice under a reduced pressure such that volatile substances are removed.

In certain embodiments, the polypeptide and lipophilic moiety conjugate is a PAR1, PAR2, PAR3, or PAR4 pepducin compound. In certain embodiments, the polypeptide is a fragment derived from PAR1, PAR2, PAR3, or PAR4, i1, i2, i3, i4 intracellular loops. In certain embodiments, the polypeptide is a fragment derived from a GPCR i1, i2, i3, i4 intracellular loops. In certain embodiments, the GPCR is a member of the Rhodopsin family.

In certain embodiments, the micelle particles are made by the process of freezing an aqueous solution comprising palmitate-KKSRALF-$NH_2$ and ammonium acetate providing ice, and placing the ice under a reduced pressure such that volatile substances are removed. In certain embodiments, the micelles are made by the process of freezing an aqueous solution comprising palmitate-KKSRALF-$NH_2$ and sorbitol providing ice, and placing the ice under a reduced pressure such that volatile substances are removed. In certain embodiments, the micelles are made by the process of freezing an aqueous solution comprising palmitate-KKSRALF-$NH_2$ and ethanol providing ice, and placing the ice under a reduced pressure such that volatile substances are removed.

In certain embodiments, the micelles are less than 0.22 microns in diameter or have an average diameter of about 200 A (angstroms), 100 A, 90 A, 80 A, 70 A, 60 A, 50 A, 45 A, 40 A, 35 A, or 30 A or small than 30 A.

In certain embodiments, the pharmaceutical composition further comprises a second anti-platelet or anti-coagulant agent. In certain embodiments, the second anti-platelet agent is selected from a cyclooxygenase inhibitor, aspirin, adenosine diphosphate (ADP) receptor inhibitor clopidogrel, prasugrel, ticagrelor, ticlopidine, phosphodiesterase inhibitor, cilostazol, glycoprotein IIB/IIIA inhibitor, abciximab, eptifibatide, tirofiban, adenosine reuptake inhibitor, dipyridamole, thromboxane inhibitor, thromboxane synthase inhibitor, thromboxane receptor antagonist terutroban.

In certain embodiments, the disclosure relates to methods of managing blood clotting, or methods of treating or preventing a blood clot, or diseases or conditions associated with undesirable clot formation comprising administering an effective amount of a pharmaceutical composition disclosed herein to a subject in need thereof.

In certain embodiments, one administers about or greater than 3 mg of water soluble micelle particles comprising palmitate-KKSRALF-$NH_2$ acetic acid salts per kg of a subject to less than or about 6 mg per kg. Typically this is done within a one hour period or two hour period.

In certain embodiments, one administers micelles comprising palmitate-KKSRALF-$NH_2$ acetic acid salts in an amount that provides a blood plasma concentration of between about 20 µmol/L to 1 µmol/L or 15 µmol/L to 4 µmol/L.

In certain embodiments, one administers micelles comprising palmitate-KKSRALF-$NH_2$ acetic acid salts in an amount that provides a blood plasma concentration of less than 20 mg/L, 10 mg/L, 5 mg/L or 3 mg/L.

In certain embodiments, the subject is a human. In certain embodiments, the subject is, is about to, or previously participated in an angioplasty or other percutaneous coronary intervention.

In certain embodiments, the subject is diagnosed with an acute coronary syndrome, atherothrombotic disease, or myocardial infarction.

In certain embodiments, the pharmaceutical composition is administered in combination with a second anti-platelet agent such as a cyclooxygenase inhibitor, aspirin, adenosine diphosphate (ADP) receptor inhibitor clopidogrel, prasugrel, ticagrelor, ticlopidine, phosphodiesterase inhibitor, cilostazol, glycoprotein IIB/IIIA inhibitor, abciximab, eptifibatide, tirofiban, adenosine reuptake inhibitor, dipyridamole, thromboxane inhibitor, thromboxane synthase inhibitor, thromboxane receptor antagonist terutroban.

In certain embodiments, the disclosure contemplates methods disclosed herein further comprising the step of administering a PAR1 or ristocetin agonists, e.g., the PAR1 agonist is SFLLRN (SEQ ID NO:1), to counteract the anti-platelet effects of the polypeptide and lipophilic moiety conjugate, e.g., in vivo and ex vivo assay systems.

DETAILED DISCUSSION

Terms

Figure 1:
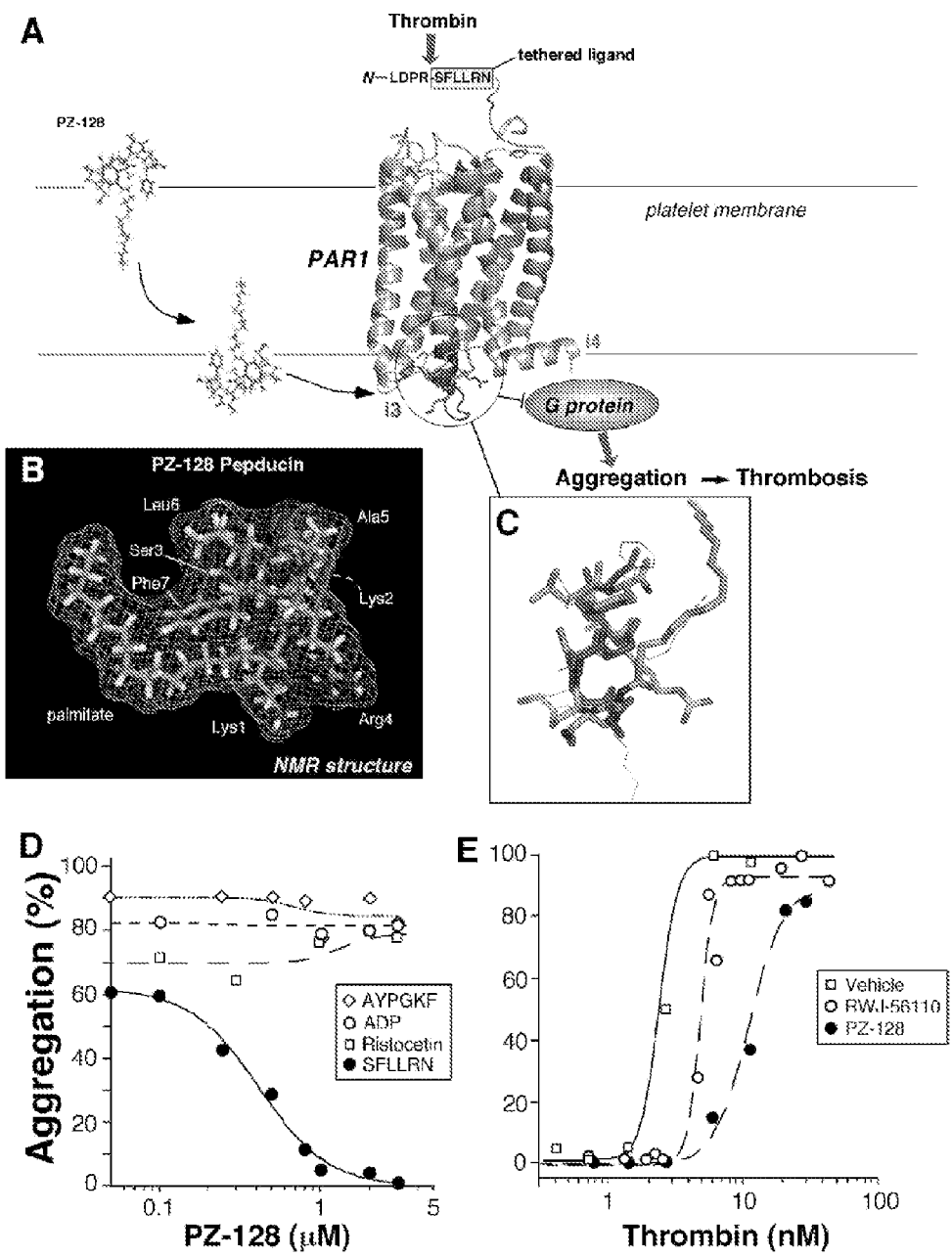
FIG. 1 shows structure and anti-platelet effects of the cell-penetrating PAR1 pepducin compound, PZ-128. A, Depiction of the mechanism of action of the cell-penetrating PZ-128 pepducin compound targeting the third intracellular loop (red) of PAR1. B, The NMR structure of PZ-128 was determined by simulated annealing methods using 210 distance restraints and included restraints to the proximal 3 hydrocarbons of the lipid. C, PZ-128 (green) had an RMSD of 1.4 Å with the corresponding peptide backbone region of PAR1 (red) residues 307-313 modeled on the 2.8 Å x-ray structure of rhodopsin in the off-state. D, PZ-128 inhibits PAR1-dependent platelet aggregation. Gel filtered human platelets were treated with various concentrations of PZ-128 and then challenged with the PAR1 agonist SFLLRN (2.5 µM), 20 µM ADP, 200 µM AYPGKF or 1 mg/ml Ristocetin. E, Human platelets were treated with 3 µM PZ-128, 3 µM RWJ-56110, or 5% dextrose vehicle before the addition of various concentrations of thrombin (n=3-5).

Unless defined otherwise, all technical and scientific terms used herein have the same meaning as is commonly understood by one of skill in the art. The following definitions are provided to help interpret the disclosure and claims of this application. In the event a definition in this section is not consistent with definitions elsewhere, the definition set forth in this section will control.

As used herein, "pepducin compounds" are cell-penetrating peptides that act as intracellular agonists or antagonist of signal transference from receptors to G proteins. Pepducin compounds utilize lipidated fragments of intracellular G protein-coupled receptor loops to modulate GPCR action in targeted cell-signaling pathways. A pepducin compound comprises a short polypeptide derived from a GPCR intracellular loop tethered to a hydrophobic moiety. This structure allows pepducin compounds to anchor in the cell membrane lipid bilayer and target the GPCR/G protein interface via a unique intracellular allosteric mechanism. Examples of pepducin compounds are described in U.S. Patent Publication US2007/0179090, the contents of which are hereby incorporated herein by reference in its entirety.

Palmitate KKSRALF-NH2 refers to the molecule with the following formula:

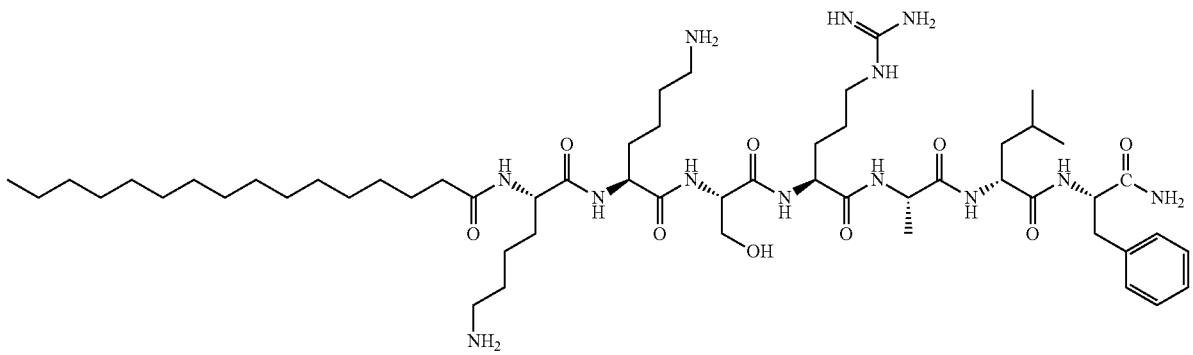 [SMILES: CCCCCCCCCCCCCCCC(=O)N[C@@H](CCCCN)C(=O)N[C@@H](CCCCN)C(=O)N[C@@H](CO)C(=O)N[C@@H](CCCNC(=N)N)C(=O)N[C@@H](C)C(=O)N[C@H](CC(C)C)C(=O)N[C@@H](Cc1ccccc1)C(N)=O]

The terms "palmitate-KKSRALF-NH$_2$ acetic acid salts" with regard to a molecular weight refer to the molecular weight of palmitate-KKSRALF-NH$_2$ plus acetic acid counterions.

"Subject" means any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, the term "about" or "approximately" when used in conjunction with a number refers to any number within 5, 10 or 15% of the referenced number.

As used herein the terms "administration," "administering," or the like, when used in the context of providing a pharmaceutical composition to a subject generally refers to providing to the subject one or more pharmaceutical compositions comprising the agent, e.g., micelle particles of PZ-128, in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery.

As used herein, an "anti-platelet" agent refers to members of a class of pharmaceuticals that decreases platelet aggregation. Non-limiting examples of anti-platelet drugs include, for example, cyclooxygenase inhibitors, adenosine diphosphate (ADP) receptor inhibitors, phosphodiesterase inhibitors, glycoprotein IIB/IIIA inhibitors and adenosine reuptake inhibitors.

As used herein, an "anti-coagulant" agent refers to drugs that prevent coagulation; i.e. that stop blood from clotting. Non-limiting examples of anti-coagulants that may be used in this invention include, for example, coumarins, vitamin K antagonists, warfarin (Coumadin, Acenocoumarol, Phenprocoumon) and synthetic pentasaccharide inhibitors of factor Xa (Fondaparinux or Idraparinux).

The term "polypeptide" refers to any chain or chains of two or more amino acids, and does not refer to a specific length of the product. A "peptide" or "polypeptide" as used herein, may be derived from a natural biological source, synthesized, or produced by recombinant technology. It may be generated in any manner, including by chemical synthesis. In accordance with this definition, a "polypeptide" may be of a size of about 3 or more, about 5 or more, about 10 or more, about 20 or more, about 25 or more, about 50 or more, about 75 or more, about 100 or more, about 200 or more, about 500 or more, about 1,000 or more, or about 2,000 or more amino acids. One or more of the amino acids may be modified, for example, by the addition of a chemical entity such as a carbohydrate group, a phosphate group, a farnesyl group, an isofamesyt group, a fatty acid group, an acyl group (e.g., acetyl group), a linker for conjugation, functionalization, or other known protecting/blocking groups. A "polypeptide," as used herein, may be fragments, derivatives, analogs, or variants of the foregoing polypeptides, and any combination thereof. Fragments of polypeptides, as that term or phrase is used herein, include proteolytic fragments, as well as deletion fragments. Variants of polypeptides include fragments and polypeptides with altered amino acid sequences due to amino acid substitutions, deletions, or insertions. Variants may occur naturally or be non-naturally occurring. Examples include fusion proteins, polypeptides having one or more residues chemically derivatized by reaction of a functional side group, and peptides that contain one or more naturally occurring amino acid derivatives of the twenty standard amino acids. These modifications may also include the incorporation of D-amino acids, or other non-encoded amino-acids. None of the modifications should substantially interfere with the desired biological activity of the peptide.

Micelles of Polypeptide and Lipophilic Moiety Conjugates

In certain embodiments, the disclosure contemplates micelle particles of polypeptide and lipophilic moiety conjugates in substantially pure form and their preparation. Stored polypeptide and lipophilic moiety conjugates have a tendency to degrade over time. Certain micelle compositions disclosed herein have superior stabilization properties due to the manner in which they are prepared.

Aqueous pharmaceutical compositions comprising PZ-128 (e.g. micelles of palmitate-KKSRALF-NH$_2$ acetic acid salts) can take several different forms, e.g., aggregates and particle forms, and sizes due to the presence of surrounding water, acidic condition, and added excipients. Aggregate and particle forms alter stability. For the purpose of administering the pharmaceutical composition to a subject, it is important that the particle sizes and makeup are consistent and substantially similar so that the pharmacokinetic profile after administration is not altered when exposed to components in blood serum.

In certain embodiments, the polypeptide and lipophilic moiety conjugates are pepducin compounds. Pepducin compounds comprise a lipophilic moiety attached to a peptide derived from the first intracellular (i1) loop structure, the second intracellular (i2) loop, the third intracellular loop (i3), or the fourth intracellular loop (i4) or fragment of a GPCR. The lipophilic moiety is a naturally or non-naturally occurring cell-penetrating and/or membrane-tethering hydrophobic moiety. Pepducin compounds may be agonists and/or antagonists of receptor-G protein signaling. These compositions exhibit selectivity for their cognate receptor.

GPCRs are typical characterized by seven clusters of hydrophobic amino acid residues, or transmembrane regions (TMs, the 7 transmembrane regions are designated as TM1, TM2, TM3, TM4, TM5, TM6, and TM7), that are located in the primary structure and pass through (span) the cell membrane. The TM regions are believed to represent transmembrane alpha-helices connected by intracellular loops (e.g. i1, i2, and i3) and extracellular loops (e1, e2, and e3). GPCRs also contain amino (N)- and carboxyl (C)-terminal domains (Palczewski et al, Science 289, 739-45 (2000)). The sequences between the transmembrane regions correspond to GPCR loops, and the location of a loop within a cell determines whether it is an intracellular or an extracellular loop. Most GPCRs have single conserved cysteine residues in each of the first two extracellular loops which form disulfide bonds that are believed to stabilize functional protein structure.

G protein coupled receptors (GPCRs) includes the luteinizing hormone receptor; the follicle stimulating hormone receptor; a thyroid stimulating hormone receptor; a calcitonin receptor; a glucagon receptor; a glucagon-like peptide 1 receptor (GLP-I); a metabotropic glutamate receptor; a parathyroid hormone receptor; a vasoactive intestinal peptide receptor; a secretin receptor; a growth hormone releasing factor (GRF) receptor; protease-activated receptors (PARs); cholecystokinin receptors; somatostatin receptors; melanocortin receptors; ADP receptors; adenosine receptors; thromboxane receptors; platelet activating factor receptor; adrenergic receptors; 5-HT receptors; chemokine receptors; neuropeptide receptors; opioid receptors; parathyroid hormone (PTH) receptor; or a vasoactive intestinal peptide (VIP) receptor.

In certain embodiments, contemplated pepducin compounds contain an amino acid sequence or fragment of a protease-activated receptor (PAR) or a chemokine receptor.

The protease-activated receptor may be, e.g., PAR1, PAR2, PAR3, or PAR4. A chemokine receptor may be a CC or CXC receptor such as CCR1, CCR2, CCR3, CCR4, CCR5, CCR6, CCR7, CCR8 or CCR9; or CXCR1, CXCR2, CXCR3, CXCR4, CXCR5, CXCR6 or CX3CR1.

The Human PAR family includes PAR-1 (Genbank Accession Number AF019616); PAR2 (Genbank Accession Number XM-003671); PAR3 (Genbank Accession Number NM-0041101); and PAR4 (Genbank Accession Number NM-003950.1), the sequences of which are hereby incorporated by reference. The human PAR-1 polypeptide sequence has Genbank Accession No. NP_001983, which is also incorporated herein by reference In certain embodiments, the lipophilic moiety is attached at the N-terminal end, the C-terminal end, an amino acid between the C-terminal amino acid and the N-terminal amino acid, or both the N-terminal and C-terminal ends of the first domain. Desirably, the cell-penetrating and/or membrane-tethering hydrophobic moiety is a lipid such as a straight chain fatty acid, e.g., nonanoyl (C9); capryl (C10); undecanoyl (C11); lauroyl (C12); tridecanoyl (C13); myristoyl (C14); pentadecanoyl (C15); palmitoyl (C16); phytanoyl (methyl substituted C16); heptadecanoyl (C17); stearoyl (C18); nonadecanoyl (C19); arachidoyl (C20); heniecosanoyl (C21); behenoyl (C22); trucisanoyl (C23); and a lignoceroyl (C24) moiety. The lipophilic moiety may be attached to the polypeptide with, e.g., amide bonds, sulfhydryls, amines, alcohols, phenolic groups, or carbon-carbon bonds. Particular embodiments include palmitoyl or lithocholic acid as the hydrophobic moiety. Other cell-penetrating and/or membrane-tethering hydrophobic moieties include cholesterol, phospholipids, steroids, sphingosine, ceramide, octyl-glycine, 2-cyclohexylalanine, benzolylphenylalanine, acyl groups, or fatty acids.

Examples of PAR1 pepducin compounds include those in the Table below.

| NAME | TARGET | LOOPS | Ammo ACID SEQUENCE | ATTACHED LIPID |
|---|---|---|---|---|
| Pli3pal-7 | PAR1 | i3 | KKSRALF (SEQ ID NO. 2) | palmitate |
| Pli3pal-12 | PAR1 | i3 | RCLSSSAVANRS (SEQ ID NO. 3) | palmitate |
| Pli3pal-12S | PAR1 | i3 | RSLSSSAVANRS (SEQ ID NO. 4) | palmitate |
| Pli3pal-10S | PAR1 | i3 | NRSKKSSALF (SEQ ID NO. 5) | palmitate |
| Pli1pal-11 | PAR1 | i1 | ILKMKVKKPAV (SEQ ID NO. 6) | palmitate |
| Pli2pal-7 | PAR1 | i2 | TLGRASF (SEQ ID NO. 7) | palmitate |
| Pli2pal-11 | PAR1 | i2 | LSWRTLGRASF (SEQ ID NO. 8) | palmitate |
| Pli2pal-16 | PAR1 | i2 | YPMQSLSWRTLGRASF (SEQ ID NO. 9) | palmitate |
| Pli2pal-21 | PAR1 | i2 | FLAVVYPMQSLSWRTLGRASF (SEQ ID NO. 10) | palmitate |
| Pli4pal13 | PAR1 | i4 | ASSESQRYVYSIL (SEQ ID NO. 11) | palmitate |
| Pli4pal13R | PAR1 | i4 | LISYVYRQSESSA (SEQ ID NO. 12) | palmitate |

Suppression of Arterial Thrombosis without Affecting Hemostatic Parameters

Thrombin-dependent platelet activation is heightened in the setting of percutaneous coronary interventions (PCI) and may cause arterial thrombosis with consequent myocardial necrosis. The occurrence of life-threatening arterial thrombotic events during acute coronary syndromes (ACS) and PCI are dependent on reactive platelets. Anti-platelet therapy thus plays a role in preventing stent thrombosis and periprocedural myocardial infarction (MI) in the high risk group of ACS and PCI patients. Platelets also maintain normal hemostasis and prevent hemorrhage following vascular injury. Platelet activation is initiated and perpetuated by binding of multiple agonists to specific G-protein-coupled receptors (GPCRs). Reinforcement of the adhesive contacts by activating G protein-dependent shape change, granule release, and integrins permits growth of a stable thrombus that is resistant to the high shear stress of arterial blood flow. Drugs that target the secondary thromboxane and ADP autocrine mediators of platelet thrombus formation such as aspirin and thienopyridines have proven to be beneficial. However, many patients taking these drugs still sustain thrombotic events. Thus, there is a need for improved therapeutics that inhibit platelet function. Given the high incidence of adverse effects in patients with acute coronary syndromes (ACS), there remains an unmet need for the development of therapeutics that target platelet activation without unduly affecting hemostasis.

The thrombin receptor, PAR1, is a candidate for therapeutic intervention in patients with acute coronary syndromes and chronic atherothrombotic disease. Thrombin cleaves and activates both the high affinity PAR1 and lower affinity PAR4 receptor. Thrombin inhibitors such as bivalirudin effectively suppress PAR1-dependent platelet activation in PCI patients. However, direct inhibition of thrombin may potentially facilitate bleeding in PCI patients as it also interferes with activation of the PAR4 thrombin receptor and fibrinogen-dependent hemostasis.

Two PAR1 small molecule inhibitors, vorapaxar (SCH530348) and atopaxar (E5555) have been evaluated in phase II trials and have been associated with a reduction in ischemic event occurrence. In several studies, vorapaxar reduced the occurrence of periprocedural MI when added to dual antiplatelet therapy. Similarly, atopaxar significantly reduced early ischemia. In the recently completed TRACER and TRA-2P Phase III trials, vorapaxar was found to significantly reduce the composite endpoint of death from cardiovascular causes, MI or stroke in ACS patients and in patients treated chronically for secondary prevention of atherothrombotic events. However, the limitations of vorapaxar include an extremely long pharmacodynamic (PD) half-life of up to 3 weeks and oral administration leading to a slower onset of PD effects during PCI, and an elevated risk of bleeding. The ability to rapidly and reversibly inhibit PAR1 signaling by a parenteral strategy would be an attractive option in high risk patients undergoing PCI.

PZ-128 is a cell-penetrating pepducin compound inhibitor of PAR1 which targets the receptor-G protein interface on the inside surface of platelets. The structure of PZ-128 closely resembles the predicted off-state of the corresponding juxtamembrane region of the third intracellular loop of PAR1. PZ-128 micelles rapidly and reversibly inhibit PAR1 platelet activation and arterial thrombosis in guinea pigs and primates without affecting bleeding or other coagulation parameters. These data provide support indicate PZ-128 micelles are an effective intervention of PAR1-driven arterial thrombosis in patients undergoing PCI.

The onset of action of PZ-128 micelles was rapid and suppressed PAR1 aggregation and arterial thrombosis in guinea pigs and baboons and strongly synergized with oral clopidogrel. There was full recovery of platelet function by 24 h. Importantly, PZ-128 micelles had no effect on bleeding or coagulation parameters in primates or in blood from PCI patients. The rapid onset of platelet inhibition and reversible properties of PZ-128 micelles are well suited to the acute interventional setting of PCI and may provide an alternative to long-acting small molecule inhibitors of PAR1. PZ-128 micelles do not suppress ADP, thromboxane or PAR4 responses. The inhibitory effects were fully reversible and overcome by high concentrations of PAR1 agonist even at early time points.

Contrary to potent thrombin inhibitors (e.g. bivalirudin, hirudin, argatroban, dabigatran), or factor Xa inhibitors (rivaroxaban, apixaban), reversible PAR1 inhibitors should not directly affect coagulation and increased bleeding during use. This is consistent with present studies in non-human primates. As thrombin-dependent fibrin generation is unaffected by inhibition of PAR1 and reversible PAR1 antagonists can be overcome by robust hemostatic thrombin generation, a thrombin-receptor antagonist may provide a safer therapeutic index than a thrombin or Xa inhibitor in preventing arterial thrombosis. Likewise, the PZ-128 micelles had no adverse effects on bleeding, coagulation, or clotting time in non-human primates and human blood samples.

Micelles of PZ-128 did not impact initial platelet adhesion to exposed collagen surfaces, but prevented large occlusive thrombi from forming. Although it is not intended that embodiments of this disclosure be limited by any particular mechanism, these findings support the notion that PAR1 inhibitors can permit the formation of an initial platelet-fibrin monolayer necessary for control of hemostasis, but still block pathological thrombus propagation that occurs at the site of endothelial denudation.

PAR1 small molecule inhibitor, vorapaxar, was recently shown to significantly increase the rate of moderate and severe bleeding in both ACS patients and in patients being treated for secondary prevention of atherothrombotic events. Two possible explanations for the elevated bleeding include: 1) the extremely long pharmacodynamic effect of vorapaxar which significantly inhibits platelet function for up to 3 weeks (plasma half-life of 5-11 days) with a single loading dose; 2) vorapaxar was administered daily for a median time of 1-2.5 years in combination with both aspirin and a P2Y12 inhibitor. In a subgroup analysis of TRACER, it was found that Vorapaxar did not increase the hazard of GUSTO moderate or severe bleeding in the patients who did not receive a thienopyridine. Therefore, it is likely that concomitant blockade of P2Y12 and thromboxane receptors along with PAR1 may also contribute to the observed bleeding risk in the ACS patients. As a much shorter-acting and reversible PAR1 antagonist PZ-128 (plasma half-life of 50-80 min) helps mitigate any untoward periprocedural bleeding in the context of dual anti-platelet therapy. Moreover, small molecule inhibitors such as vorapaxar and atopaxar interact with the ligand binding site on the extracellular surface of the receptor. By comparison, PZ-128 micelles work by an entirely different mechanism of action on the inner surface of the lipid bilayer where it modulates the interactions of PAR1 with intracellular G proteins.

The structure of PZ-128 was found to closely resemble the predicted off-state of the corresponding juxtamembrane region of the third intracellular loop and helix 6 region of PAR1, consistent with a mechanism whereby PZ-128 may stabilize or mimic the off-state of PAR1. Intervention of PAR1-dependent platelet activation with the PZ-128 micelles thus represents an improved therapeutic strategy for suppressing arterial thrombosis, which could potentially benefit PCI patients being treated for severe atherothrombotic heart disease.

Pharmaceutical Compositions

In certain embodiments, the disclosure relates to pharmaceutical composition comprising micelle particles disclosed herein and a pharmaceutically acceptable excipient. Micelles comprising polypeptide and lipophilic moiety conjugate salts, e.g., Palmitate-KKSRALF-NH$_2$ micelle particles made up of pharmaceutically acceptable salts are also useful in the method of the disclosure and in pharmaceutical compositions of the disclosure. The pharmaceutical compositions of the present disclosure can be administered to subjects either orally, rectally, parenterally (intravenously, intramuscularly, or subcutaneously), intracisternally, intravaginally, intraperitoneally, intravesically, locally (powders, ointments, or drops), or as a buccal or nasal spray.

In certain embodiments, the disclosure relates to micelles comprising polypeptide and lipophilic moiety conjugate salts, e.g., micelle particles comprising palmitate-KKSRALF-NH$_2$ salts wherein the counterion is selected from adipic acid, camphoric acid, carbonic acid, cinnamon acid, citric acid, fumaric acid, galactaric acid, gentisic acid, glucaric acid, glucoheptonic acid, D-gluconic acid, D-glucuronic acid, gluataric acid, alpha-oxo-glutaric acid, lactobionic acid, maleic acid, L-malic acid, malonic acid, pamoic acid, pyruvic acid, salicylic acid, sebacic acid, succinic acid, tartaric acid, or combinations thereof.

In certain embodiments, the disclosure relates to palmitate-KKSRALF-NH$_2$ salts wherein the counterion is ascorbic acid or acetic acid. In certain embodiments, the salt may be in a composition optionally comprising sodium ion, ammonium, imidazole or combinations thereof.

In certain embodiments, the disclosure relates to pharmaceutical compositions comprising palmitate-KKSRALF-NH$_2$ salts in combination with mannitol, glucuronic acid, or combinations thereof.

Micelle particles suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate. Proper fluidity can be maintained, for example, by the use of a coating such as lecithin, by the maintenance of the required particle size in the case of dispersions and by the surfactants. These compositions may also contain adjuvants such as preserving, emulsifying, and dispensing agents. Prevention of the action of microorganisms be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the micelle particles are admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar and as high molecular weight polyethylene glycols, and the like.

Solid dosage forms such as tablets, dragees, capsules, pills, and granules can be prepared with coatings and shells, such as enteric coatings and others well known in the art. They may contain opacifying agents, and can also be of such composition that they release palmitate-KKSRALF-NH$_2$ or salts in a certain part of the intestinal tract in a delayed manner. Examples of embedding compositions which can be used are polymeric substances and waxes. The micelle particles can also be used in micro-encapsulated form, if appropriate, with one or more of the above-mentioned excipients. Controlled slow release formulations are also preferred, including osmotic pumps and layered delivery systems.

Liquid dosage forms for oral administration include pharmaceutically acceptable emulsions, solutions, suspensions, syrups, and elixirs. In addition to the micelles comprising polypeptide and lipophilic moiety conjugate salts, e.g., palmitate-KKSRALF-NH$_2$ salts, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, viscoleo, castor oil and sesame oil, glycerol, tetrahydrofurfuryl alcohol, poly ethylene glycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents. Suspensions, in addition to micelles comprising polypeptide and lipophilic moiety conjugate salts, e.g., palmitate-KKSRALF-NH$_2$ salts, may contain suspending agents, as for example, ethoxylated iso-stearyl alcohols, polyoxyethylene sorbitol and sorbitan esters, microcrystalline cellulose, aluminum metahydroxide, bentonite agar-agar and tragacanth, or mixtures of these substances, and the like.

Pharmaceutical compositions disclosed herein can be in the form of pharmaceutically acceptable salts, as generally described below. Some preferred, but non-limiting examples of suitable pharmaceutically acceptable organic and/or inorganic acids are acetic acid, hydrochloric acid, hydrobromic acid, sulfuric acid, nitric acid, and citric acid, adipic acid, camphoric acid, carbonic acid, cinnamon acid, citric acid, fumaric acid, galactaric acid, gentisic acid, glucaric acid, glucoheptonic acid, D-gluconic acid, D-glucuronic acid, gluataric acid, alpha-oxo-glutaric acid, lactobionic acid, maleic acid, L-malic acid, malonic acid, pamoic acid, pyruvic acid, salicylic acid, sebacic acid, succinic acid, tartaric acid, or combinations thereof.

Pharmaceutically acceptable salts of polypeptide and lipophilic moiety conjugates, e.g., palmitate-KKSRALF-NH$_2$, include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases can also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

Polypeptide and lipophilic moiety conjugate salts, e.g., Palmitate-KKSRALF-NH$_2$ salts described herein, can be administered in the form of prodrugs. A prodrug can include a covalently bonded carrier which releases the active parent drug when administered to a mammalian subject. Prodrugs can be prepared by modifying functional groups present in palmitate-KKSRALF-NH$_2$ in such a way that the modifications are cleaved, either in routine manipulation or in vivo, to the parent compounds. Prodrugs include, for example, wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in palmitate-KKSRALF-NH$_2$. Examples of structuring a compound as prodrugs can be found in the book of Testa and Caner, Hydrolysis in Drug and Prodrug Metabolism, Wiley (2006) hereby incorporated by reference. Typical prodrugs form the active metabolite by transformation of the prodrug by hydrolytic enzymes, the hydrolysis of amides, lactams, peptides, carboxylic acid esters, epoxides or the cleavage of esters of inorganic acids.

Pharmaceutical compositions typically comprise an effective amount of micelles particles of polypeptide and lipophilic moiety conjugate salts, e.g., palmitate-KKSRALF-NH$_2$ salts and a suitable pharmaceutical acceptable carrier. The preparations can be prepared in a manner known per se, which usually involves mixing micelles with the one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences. Ester prodrugs are readily degraded in the body to release the corresponding alcohol. See e.g., Imai, Drug Metab Pharmacokinet. (2006) 21(3): 173-85, entitled "Human carboxylesterase isozymes: catalytic properties and rational drug design.

In certain embodiments, for pharmaceutical use, micelle particles of palmitate-KKSRALF-NH$_2$ salts can be formulated as a pharmaceutical preparation comprising palmitate-KKSRALF-NH$_2$ salts and at least one pharmaceutically acceptable carrier, diluent or excipient and/or adjuvant, and optionally one or more further pharmaceutically active compounds. The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, micelle particles of palmitate-KKSRALF-NH$_2$ salts of the disclosure e.g., about 10, 25, 50, 100, 200, 300 or 400 mg per unit dosage.

The micelle particles will generally be administered in an "effective amount," by which it is meant any amount of palmitate-KKSRALF-NH$_2$ salts disclosed herein that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the subject per day, more often between 0.1 and 500 mg, such as between 1 and 250 mg, for example about 5, 10, 20, 50, 100, 150, 200 or 250 mg, per kilogram body weight of the subject per day, which can be administered as a single daily dose, divided over one or more daily doses. The amount(s) to be administered, the route of administration and the further treatment regimen can be determined by the treating clinician, depending on factors such as the age, gender and general condition of the subject and the nature and severity of the disease/symptoms to be treated. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

EXPERIMENTAL

The following is intended to provide examples on methods of making and using embodiments of the disclosure. It is not intended to limit the scope.

Formulating Substantially Pure Aqueous PZ-128 Micelle Solutions

PZ-128 (palmitate-KKSRALF-NH$_2$) initially was synthesized by standard Fmoc solid phase methods to provide the amide terminal conjugate and purified to 99.1% by reverse-phase high-performance liquid chromatography. Crude PZ-128 (10 mg-trifluoroacetate (TFA) salt) was dissolved in 200 µL of dimethylsulfoxide (DMSO). Removing TFA was done by the following procedure: condition Sep-Pak classic C-18 reversed-phase cartridge (Cat.WAT051910, Waters, Millipore) or other reverse phase columns with a) 20 mL 100% methanol b) 10 mL 100% acetonitrile c) 20 mL of 10% methanol and 90% water/10 mM Ammonium Acetate; load peptide solution into the reversed phase cartridge; develop with a) 5 ml of 10% methanol and 90% water/10 mM Ammonium Acetate b) 5 ml of 20% Acetonitrile and 80% water/10 mM Ammonium Acetate c) 5 ml of 40% Acetonitrile and 60% water/10 mM Ammonium Acetate; 5 ml of 60% Acetonitrile and 40% water/10 mM Ammonium Acetate; and collect 5 mL fractions a) to d) in separate 15 mL polycarbonate Falcon tubes and analyze each fraction for peptide content and purity by MALDI mass spectrometry.

The yield and purity of the eluted PZ-128 product were compared from three different cartridges (Waters Classic C18 reversed phase cartridge [186000132], Oasis® HLB Plus Cartridge [WAT051910] and Sep-Pak® TC2 cartridge). The highest amount of PZ-128 product was recovered from the 40% acetonitrile/60% water/10 mM ammonium acetate fraction in all 3 cartridges. The PZ-128 had a low yield (30% recovery) with the Oasis® HLB Plus Cartridge and was increased to 60% yield with the Waters Classic C18 cartridge and Sep-Pak® TC2 cartridge. Higher yields and purities were obtained using high performance reversed phase chromatography. The PZ-128 in the 40% acetonitrile/ 60% water/10 mM ammonium acetate fraction was the purest by MALDI mass spectrometry using the Waters Classic C18 cartridge. In certain embodiments, the disclosure contemplates methods comprising purifying a polypeptide and lipophilic moiety conjugate with about a 40% acetonitrile/60% water/10 mM ammonium acetate solution.

Column recovered fractions containing PZ-128 ammonium salts were lyophilized by using the following procedure: 5 mL of elute from reverse phase column cartridge was place into a 15-mL vial; the sample frozen in dry ice-isopropanol bath for 5 minutes with swirling until completely frozen, the temperature should be about −35 to −45° C. and the vacuum pressure should be about 60-100×10$^{-3}$ mBar; frozen samples/vials are places in a 0.5-1 L lyophilization glass container; open the chamber to the vacuum pump where the vacuum pressure should rise and then come back to 100-200×10$^{-3}$ M Bar until drying is complete; and the sample is stored at −20° C. The product of the first PZ-128 lyophilization was dissolved in pure water and lyophilized a second time. The products of the second PZ-128 lyophilization did not solubilize (5 mg/mL) in any of the above formulations including 100% water.

To increase the solubility of PZ-128 after the second lyophilization, a series of excipients were added to the 100% water used to dissolve the product of the first lyophilization. Formulations including 100% water, 12% captisol/82% water, 50% captisol/50% water, 6% ethanol/94% water, 100% ethanol, 10% Tween-80/90% water, 20% Tween-80/80% water, 10% PEG400/90% water, 40% acetonitrile/60% water/10 mM ammonium acetate, 100% methanol and 5% PEG400/45% water/50% ethanol.

The different excipients listed in Table 1 were added to 10×500 μL aliquots of the fully soluble 1 mg/mL PZ-128 solution (product of the first lyophilization), mixed, froze, and lyophilization overnight. After lyophilization, the appearance of the dried lyophilizate was examined and the solubility determined after reconstitution with 100 μL water to 5 mg/mL PZ-128 salt product.

The appearances of each of the samples after a second lyophilization from water with the different excipients are listed in Table 1. The lyophilized aliquots were then tested for solubility by visual inspection after reconstitution with 100% water at a final concentration of 5 mg/mL as shown in Table 1.

TABLE 1

Excipients added prior to 2nd lyophilization, resulting appearance of 2nd lyophilizate, and solubility of PZ-128 after reconstitution in water at 5 mg/mL.

| Exp # | CH$_3$COONH$_4$ 1M | PEG400 100% | Tween 80 20 % | Sorbitol 5% | Ethanol 100% | Appearance alter lyophilization | Solubility |
|---|---|---|---|---|---|---|---|
| 1 | 5 μL | | | | | Dry powder | soluble |
| 2 | 5 μL | 10 μL | | | | clear jelly, 20 μL liquid | nonsoluble |
| 3 | | 10 μL | | | | clear jelly, 15 μL liquid | nonsoluble |
| 4 | 5 μL | | | 5 μL | | Dry powder | soluble |
| 5 | | | | 5 μL | | Small clear ppt | particles |
| 6 | 5 μL | | 100 μL | | | yellow jelly, 25 μL liquid | nonsoluble |
| 7 | | | 100 μL | | | yellow jelly, 25 μL liquid | nonsoluble |
| 8 | 5 μL | | | | 10 μL | Dry powder | soluble |
| 9 | | | | | 10 μL | Dry powder | soluble |
| 10 | | | | | 25 μL | Dry powder | particles |

According to Table 1, the addition of ammonium acetate, ammonium acetate plus sorbitol, ammonium acetate plus ethanol or ethanol alone into the PZ-128 solution after the first lyophilization maintained the solubility of the final PZ-128 substance in water.

A filter sterilization step was added just prior to the second lyophilization, i.e., filtering through a 0.22 micron PVDF filter before the second lyophilization. Filtering the solution by using 0.22 micron pore filter was used to create sterile monodispersed micelle particles. Micelles of PZ-128-ammonium acetate salts obtained after a second lyophilization were readily soluble in 100% water and 5% dextrose/water at 5 mg/mL.

Biocompatible PZ-128 in Micellular Form

Figure 6:
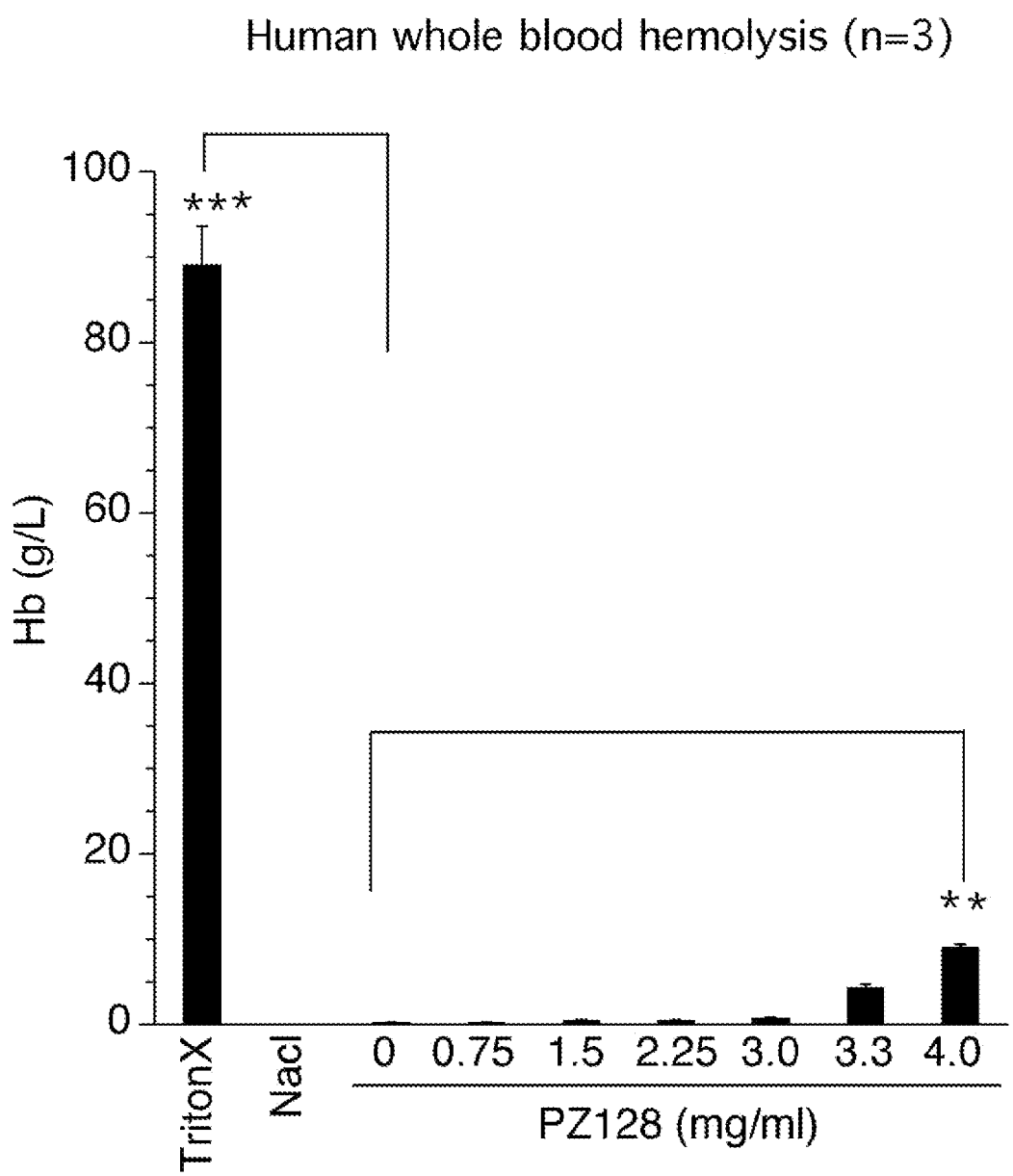
FIG. 6 shows data indicating there was no significant hemolysis of human whole blood at up to 3.3 mg/mL PZ-128. Fresh human whole blood (anticoagulated with 10 U heparin/mL) was mixed 2:1 with the various indicated dilutions of micelles of PZ-128 in 5% dextrose, incubated for 40 min at 37° C., and red blood cell lysis quantified by hemoglobin (Hb) release into the supernatant.

The PZ-128 micelle particles were solubilized in 5% dextrose/water at 10 mg/mL concentration and serially diluted with additional 5% dextrose/water to make stock solutions of 0.75, 1.5, 2.25, 3.0, 3.3 and 4.0 mg/mL PZ-128 in 5% dextrose water. Fresh human whole blood (anticoagulated with 10 U heparin/mL) was mixed 2:1 with the various dilutions of PZ-128 in 5% dextrose, incubated for 40 min at 37° C., and red blood cell lysis quantified by hemoglobin (Hb) release into the supernatant. There was no significant hemolysis of human whole blood at up to 3.3 mg/mL PZ-128. The final pH of the PZ-128 micelles in 5% dextrose/water ranged from 6.75 to 7.13 at 1.25-10 mg/mL at room temperature. See FIG. 6.

NMR Structural Determination of PZ-128 in Micellular Form

NMR samples were prepared by dissolving lyophilized PZ-128 in a buffer comprising 5% glucose-d7, 6.8 mM PZ-128 (final concentration), pH 7.1 with 10% D$_2$O. Samples at acidic pH were prepared by adding perdeuterated acetic acid to 10 mM and adjusting the pH to 4.9. Spectra were collected at 25° C. on Bruker Avance-600 and AMX-500 spectrometers. 2D NOESY sand TOCSY spectra were collected using mixing times of 100 ms and 31 ms, respectively.

Structure and Anti-Platelet Activity of PZ-128 Micelles

PZ-128 is a cell-penetrating lipopeptide derived from the juxtamembrane region of the i3 loop and N-terminus of transmembrane domain 6 (TM6) of PAR1 (FIG. 1A). This region has been shown to be essential for coupling of PAR1 with associated G proteins. Incorporation of the N-terminal palmitate lipid facilitates rapid and highly efficient translocation of the pepducin compound across the plasma membrane to the inner leaflet of the lipid bilayer. The solution structure of PZ-128 was determined by NMR (FIG. 1B) and the peptide was found to form a well-defined α-helix extending from the palmitate lipid. Structural models were generated of full-length PAR1 in the off- and on-states using the refined x-ray structures of rhodopsin (1HZX) and opsin bound to the Gα C-terminal peptide (3DQB) as templates, respectively, for comparison with the NMR-derived structure of the PZ-128 peptide. PZ-128 was found to form a highly similar structure as the corresponding region of PAR1 (residues 307-313) in the off-state with a RMSD of 1.4 Å (FIG. 1C).

The PZ-128 micelles completely inhibited human platelet aggregation in response to the PAR1 agonist SFLLRN (SEQ ID NO: 1) with an IC$_{50}$ value of 0.5 μmol/L, but had no inhibitory activity against PAR4 (AYPGKF)(SEQ ID NO:

13), ADP or ristocetin agonists (FIG. 1D). PZ-128 also markedly right-shifted thrombin-induced aggregation by 5-fold. By comparison, the small molecule RWJ-56110 which antagonizes PAR1 at the extracellular ligand-binding site gave a 2-fold right shift in the thrombin activation curve of human platelets.

Figure 2:
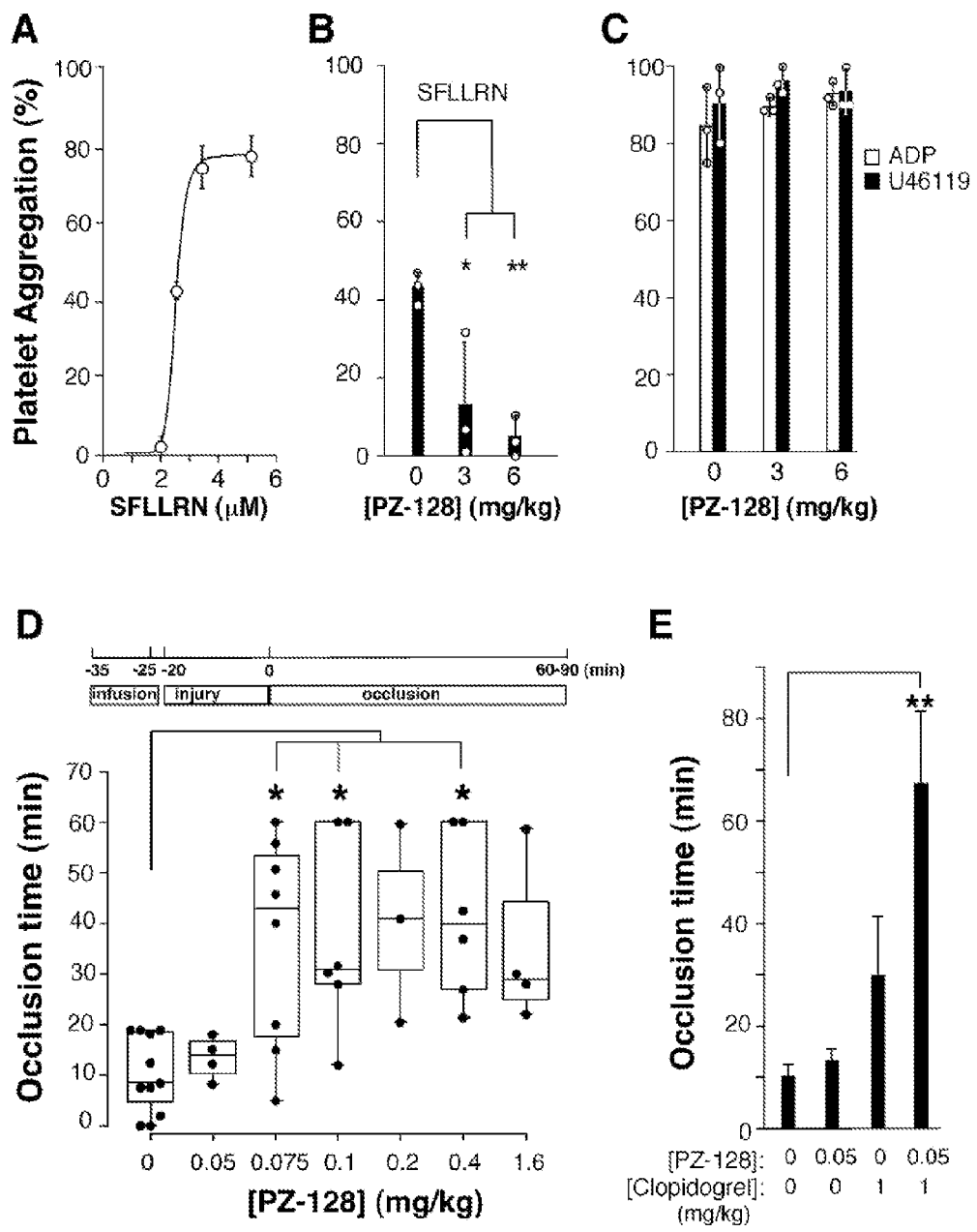
FIG. 2 shows data on the effects of PZ-128 on platelet aggregation and arterial thrombosis in guinea pig. PZ-128 or 5% dextrose USP vehicle was infused for 10 min into the jugular vein of male and female guinea pigs (0.55-0.65 kg). A-C, At the 15 min time point, whole blood was collected by cardiac puncture in 100 µg/ml PPACK/4% Na-citrate (final) anti-coagulant and platelet rich plasma (PRP) prepared and aggregation measurements were performed. (A) PRP from vehicle-treated animals (n=3) was challenged with SFLLRN to obtain an $EC_{50}$ of 2.5 µM. B-C, PRP obtained at the 15 min time point after infusion with vehicle, 3 mg/kg PZ-128 or 6 mg/kg PZ128 was challenged with 2.5 µM SFLLRN, 20 µM ADP or 20 µM thromboxane mimetic, U46119. Individual data points (n=3) are overlayed on bar graphs depicting mean±SD. D, PZ-128 was delivered by 10 min infusion, 5 min prior to initiation of FeCl injury. The time at which the blood-flow decreased to less than 0.01 volts was recorded as occlusion time of vessels. E, Observed synergistic effect of co-administration of low dose of PZ-128 (0.05 mg/kg) and clopidogrel (1 mg/kg PO 4 h prior to start of infusion) on the mean increase of occlusion time over a 90 min period (n=5). Data in B-D were analyzed by the non-parametric Kruskal-Wallis test with the Dunn's multiple pairwise comparison post-test. Data in E were analyzed by two-way ANOVA. *P<0.05, **P<0.01. Global P values were 0.044 for B, 0.33 for C, 0.018 for D, and 0.047 for E.

PZ-128 Delivered in Micelle Form Inhibits Platelet Aggregation and Arterial Thrombosis in Guinea Pigs Aside from humans and other primates, the only other animal species known to harbor PAR1 on their platelets are guinea pigs. The PAR1 agonist, SFLLRN, was confirmed to activate guinea pig platelets with an $EC_{50}$ value of 2.5 µmol/L (FIG. 2A). PZ-128 micelles were delivered by internal jugular vein infusions over 10 min. At the 15 min time point, 3 and 6 mg/kg PZ-128 provided significant, dose-dependent inhibition of ex vivo platelet aggregation to SFLLRN (FIG. 2B). PZ-128 had no effect on aggregation to ADP or the thromboxane mimetic, U46119 (FIG. 2C).

A carotid artery $FeCl_3$ injury model was used in guinea pigs to assess the anti-thrombotic efficacy of PZ-128 micelles within 15 min of initiation of drug administration. $FeCl_3$ denudes the artery and exposes type I collagen and other subendothelial matrix proteins to initiate platelet-dependent thrombosis. Guinea pigs received 10 min intravenous infusions of PZ-128 micelles, 5 min prior to carotid artery injury. There was a significant dose-dependent protection against arterial occlusion with an $EC_{50}$ of 0.075 mg/kg in guinea pig (FIG. 2D). Mean occlusion times increased by 4-fold to 40 min at doses above 0.05 mg/kg PZ-128.

The anti-thrombotic effects of PZ-128 micelles when used in combination with clopidogrel were next assessed in order to explore the possibility that dual inhibition of PAR1 and the P2Y12 ADP receptor may protect against arterial thrombosis. Sub-therapeutic doses of each drug were selected that provided non-significant protection when used alone in the guinea pigs. As shown in FIG. 2E, treatment of animals with clopidogrel and PZ-128 micelles together significantly extended the carotid artery occlusion time by at least 7-fold as compared to vehicle-treated animals. These data indicate that dual inhibition of PAR1 and P2Y12 provides strong synergistic effects in preventing carotid artery thrombosis.

PZ-128 Delivered in Micelle Form Inhibits Platelet Aggregation in Baboons

Figure 3:
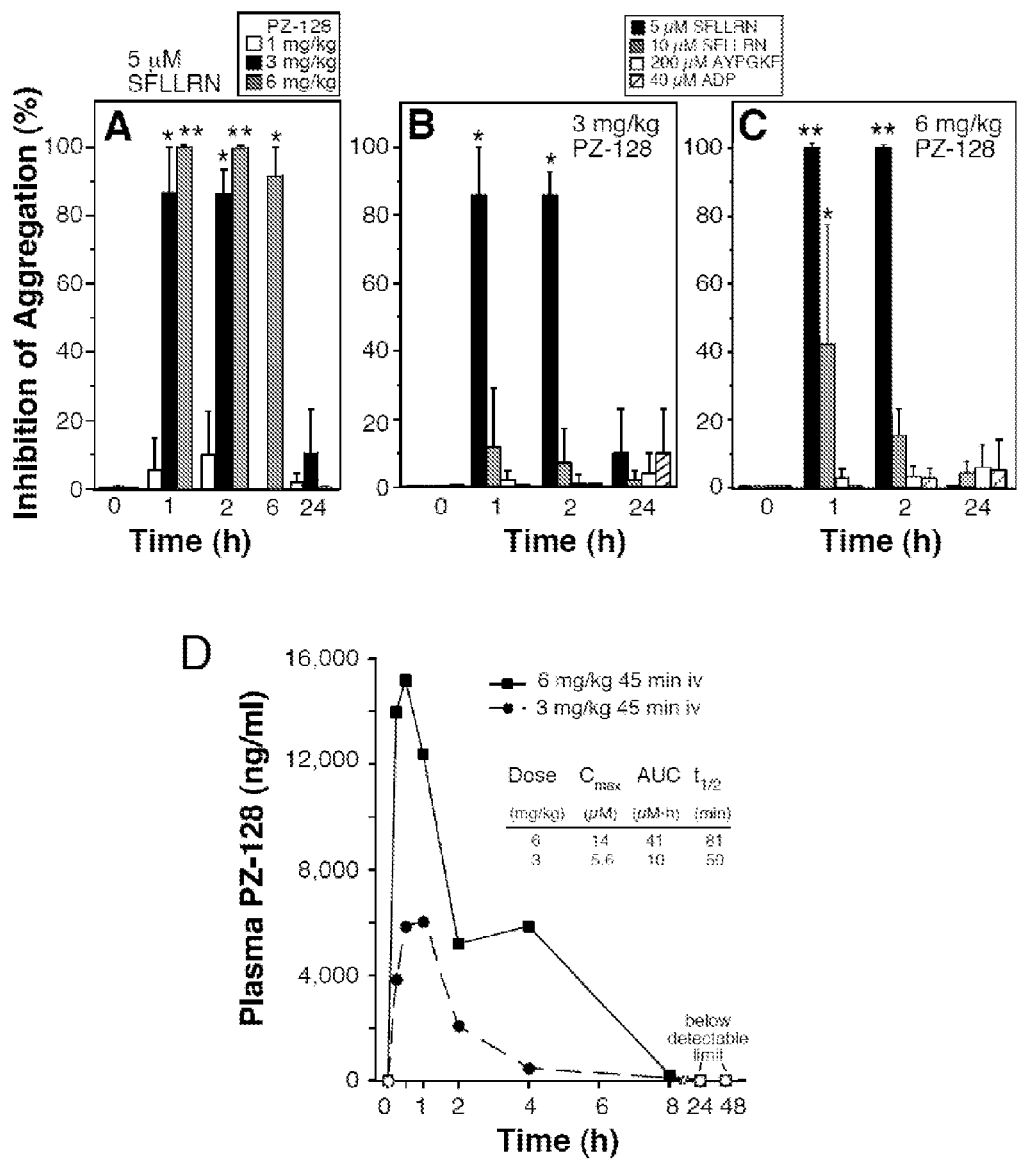
FIG. 3 shows data indicating inhibition of PAR1-dependent platelet aggregation in baboons. A-C, Male baboons (10-12 kg) were administered 1, 3 or 6 mg/kg PZ-128, or 5% dextrose USP vehicle by iv infusion and blood collected into 100 μg/ml PPACK anticoagulant at 0, 1, 2, 6, or 24 h time points. Light transmission platelet aggregometry was performed with platelet rich plasma with the indicated agonists (SFLLRN for PAR1, AYPGKF for PAR4 and ADP for P2Y12 and P2Y1). Data are reported as mean±SD (n=3-7) relative to time 0 controls (0%) and were analyzed by repeated measures one-way ANOVA with Bonferroni post-test correction; *P<0.05, **P<0.01 relative to time 0. Global P values were >0.05 for 1 mg/kg, 0.004 for 3 mg/kg, <0.0001 for 6 mg/kg. D, Pharmacokinetics of 3 and 6 mg/kg 45-min iv infusions of PZ-128 in male baboons. Plasma PZ-128 levels were measured by LC/MS/MS at 9 sequential time points: baseline, 15 min, 30 min, 1 h, 2 h, 4 h, 8 h, 24 h and 48 h after the start of infusion. Open symbols indicated plasma concentrations that were under the measurement threshold (5 ng/ml).

The anti-platelet effects of PZ-128 micelles were next examined in baboons at various time points after receiving different doses of intravenous infusions. Data from baboons showed excellent pharmacodynamic correlations with dose and time-dependent inhibition of PAR1-induced ex vivo platelet aggregation (FIG. 3). At the lowest dose tested, 1 mg/kg PZ-128 micelles (30 min infusion), PAR1-dependent aggregation (5 µM SFLLRN) was inhibited by only 5-10% at the 1-2 h time points (FIG. 3A). At the 3 mg/kg dose (30 min infusion), PAR1-dependent aggregation was inhibited by 85% at the 1 h and 2 h time points, but was not appreciably inhibited at the 24 h time point (FIG. 3B). At the 6 mg/kg dose (45 min infusion), PAR1-dependent aggregation was inhibited by 100% at 1-2 h time points, 90% at 6 h, but was completely recovered by 24 h (FIG. 3A) Inhibition of PAR1 by PZ-128 micelles was reversible, as evidenced by loss of inhibition with higher concentrations of SFLLRN agonist (10 µM) at both the 3 mg/kg and 6 mg/kg doses (FIG. 3B-C). As a further assessment of in vivo specificity, PZ-128 gave no inhibition at any dose of either the ADP or AYPGKF (PAR4) responses at any time point.

Peak plasma levels of PZ-128 in baboons were reached at 30 $min^{-1}$ h after the start of intravenous infusions at both 3 and 6 mg/kg doses. The maximal plasma concentration of PZ-128 was 14 µmol/L at the 6 mg/kg dose and 5.6 µmol/L for the 3 mg/kg dose. PZ-128 was nearly completely cleared from plasma by 8 h with a half life of 50-81 min. PZ-128 was not detectable in plasma at 24-48 h time points. The pharmacokinetic and anti-platelet pharmacodynamic properties of PZ-128 micelles indicate that this lipopeptide reaches maximal activity during and immediately after intravenous infusion and is completely eliminated by the next day.

Effect of PZ-128 Delivered in Micelle Form on Baboon Arterial Thrombosis

Figure 4:
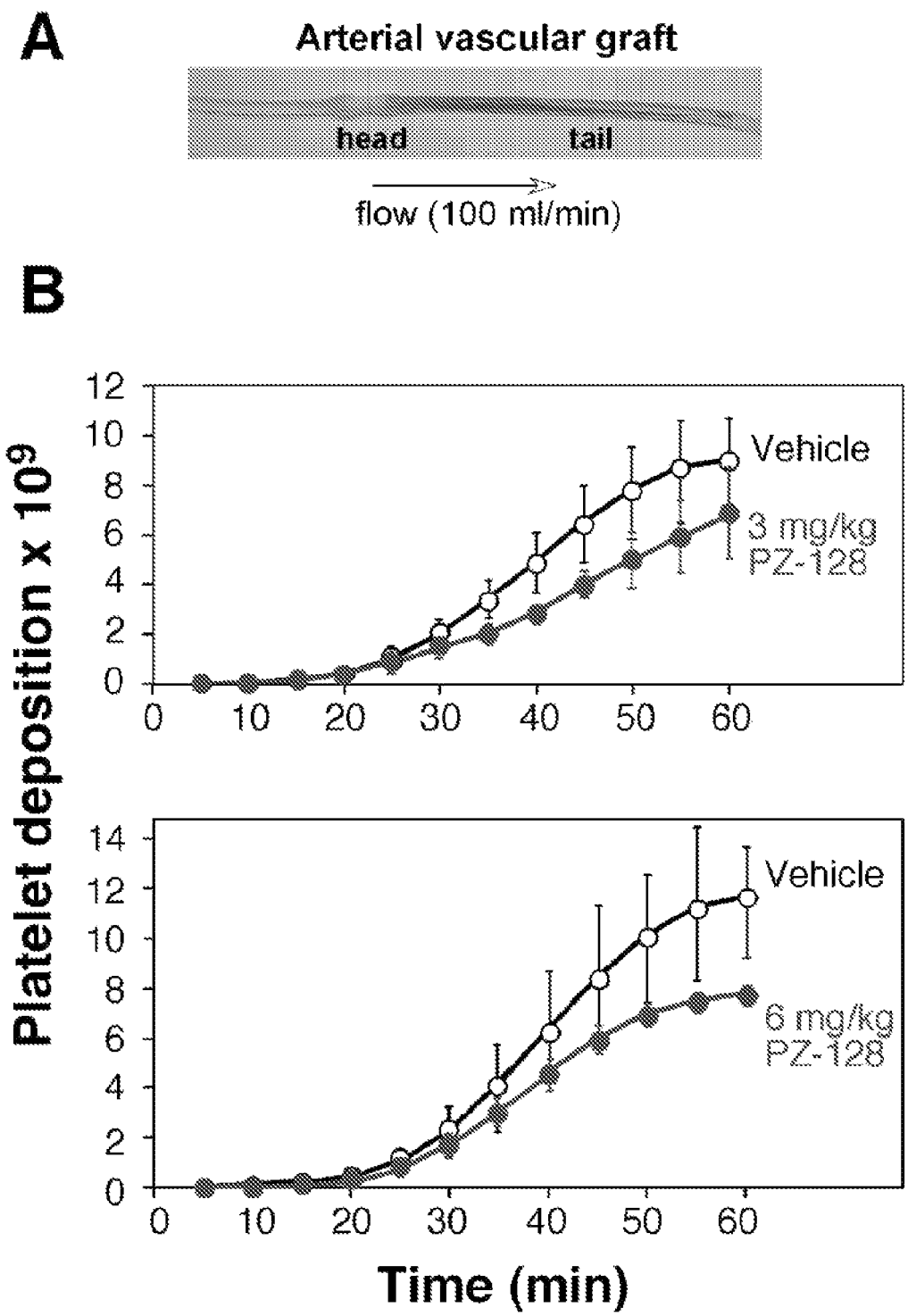
FIG. 4 shows data indicating inhibition of arterial thrombosis in baboons by PZ-128. 10-14 kg baboons were administered 3 mg/kg or 6 mg/kg PZ-128 by a 45 min iv infusion versus 5% dextrose vehicle (n=2-6). A, Net platelet accumulation was measured during the first 60 minutes of thrombus growth on a femoral arterio-venous Dacron graft (4 mm ID) inserted between silicone rubber tubing segments comprising a high-flow shunt. Blood flow was maintained at 100 ml/min by distal clamping the shunt. Autologous platelets were radiolabeled with indium-111 (1 mCi), and reinjected into the animals before thrombosis experiments. B, Deposition of platelets (mean±SD) was quantified in the head plus tail regions of the thrombus by 111Indium-labeled platelet imaging with 5-minute data acquisition periods starting at 60 min after initiation of the infusion. Statistical significance was determined using a variance stabilizing LN (natural log) transformation and a repeated measures mixed effects model with an autoregressive covariance structure. Subjects (individual baboons) were included in the model as a random effect. P=0.606 for 3 mg/kg vs vehicle and P=0.0028 for 6 mg/kg vs vehicle.

Baboon arterial thrombosis experiments were conducted to determine whether the PZ-128 micelles had the potential to inhibit arterial thrombosis in primates. An arterial-venous shunt equipped with a Dacron vascular graft with an internal lumen diameter of 4 mm at a high flow rate of 100 ml/min was used. Thrombogenesis was assessed by measuring platelet content of the head and tail regions of the developing thrombus (FIG. 4A) and quantified by $^{111}$Indium-labeled platelet imaging over 60 min. PZ-128 micelles at a dose of 1 mg/kg had no effect on platelet-thrombus deposition in the baboon. As shown in FIG. 4B, the 6 mg/kg iv infusion dose of PZ-128 micelles gave a significant protective effect against platelet arterial thrombus formation as compared to vehicle (P=0.0028). The effects of the 3 mg/kg dose were not significant but showed a tendency to be protective against arterial thrombosis. These data indicate that PZ-128 micelles can inhibit platelet-dependent thrombus formation in non-human primates under conditions of high arterial flow.

Effect of PZ-128 Delivered in Micelle Form on Hemostatic Parameters in Primates and Blood from PCI Patients Whether PZ-128 had any adverse effects on hemostasis or coagulation indices in baboons and monkeys was evaluated. At all doses tested (1-6 mg/kg), PZ-128 micelles had no effect on bleeding time, platelet counts or hematocrit in baboons (Table 2).

TABLE 2

PZ-128 Does not Enhance Bleeding Time in Baboons

| PZ-128 Dose | Baseline | 1-2 h | P value |
|---|---|---|---|
| Platelets (k/µL) | | | |
| 1 mg/kg, n = 3 | 270 ± 39 | 258 ± 44 | 0.75 |
| 3 mg/kg, n = 5 | 339 ± 74 | 334 ± 99 | 0.88 |
| 6 mg/kg, n = 4 | 286 ± 96 | 294 ± 80 | 0.63 |
| Hematocrit (%) | | | |
| 1 mg/kg, n = 3 | 39 ± 3 | 41 ± 3 | 0.25 |
| 3 mg/kg, n = 4 | 36 ± 1 | 39 ± 2 | 0.13 |
| 6 mg/kg, n = 4 | 36 ± 4 | 40 ± 4 | 0.13 |
| Bleeding time (min) | | | |
| ASA + Clopidogrel, n = 1 | 5.5 | >20 | — |
| 1 mg/kg, n = 3 | 2.8 ± 1.3 | 3.3 ± 1.2 | 0.50 |
| 3 mg/kg, n = 5 | 4.4 ± 1.9 | 4.6 ± 1.5 | 1.0 |
| 6 mg/kg, n = 3 | 4.0 ± 2.3 | 3.7 ± 1.6 | 0.59 |

PZ-128 micelles were also administered daily for 4 days to adult male and female cynomolgus monkeys with 1 h iv infusions of 3 mg/kg, 10 mg/kg and 30 mg/kg PZ-128. Coagulation parameters prothrombin time (PT) and activated partial thromboplastin time (aPTT) were unaffected in all monkeys at 3-30 mg/kg PZ-128 at either day 1 and day 5 as compared to baseline or vehicle-treated animals (Table 2). No spontaneous, venous access, or retinal bleeding was observed in any monkey (n=38) even at PZ-128 plasma levels (Cmax) exceeding 200 µM.

Figure 5:
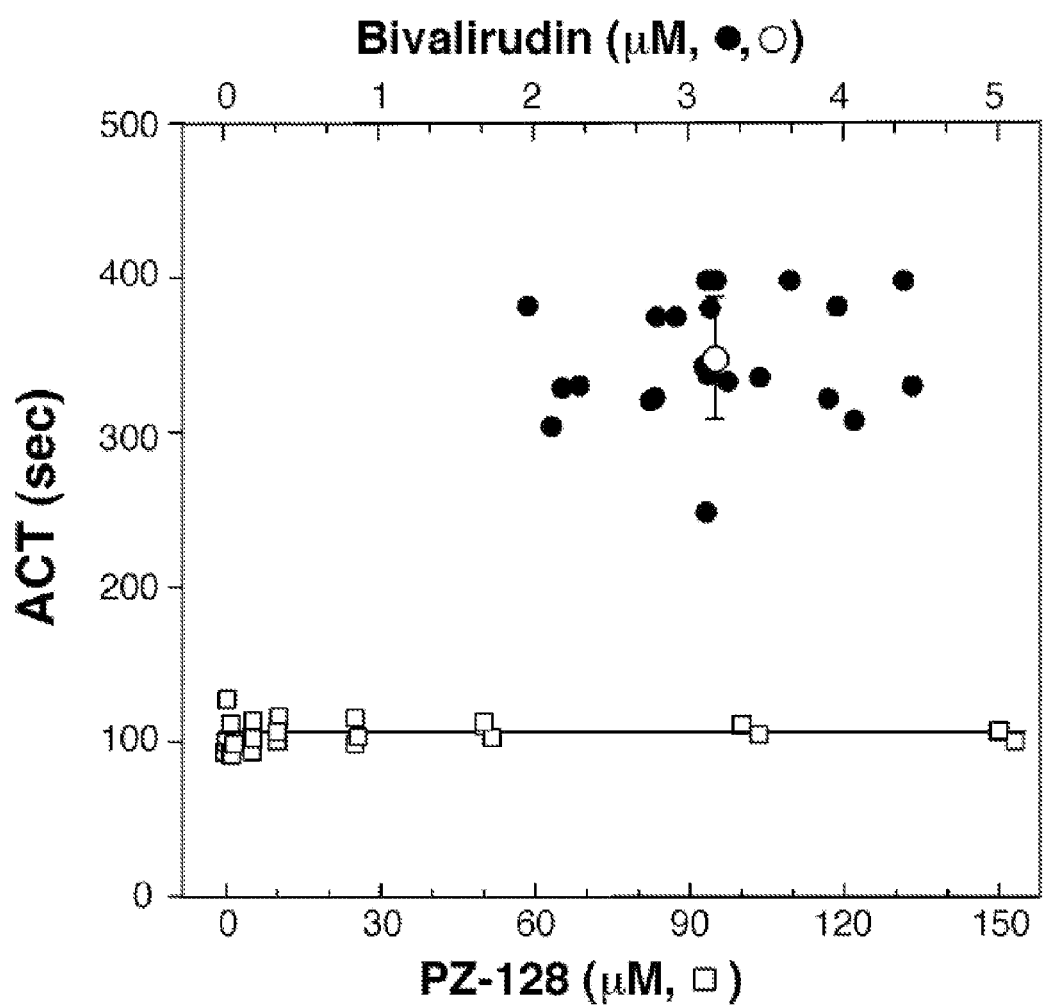
FIG. 5 shows data suggesting PZ-128 does not affect activated clotting time of blood from PCI patients. PZ-128 (χ) was spiked at various concentrations (0-150 μM) into fresh whole blood obtained from patients just prior to PCI. By comparison, blood was obtained at the 30 min time point from PCI patients (n=22) after a weight-adjusted dosage of bivalirudin (•) administered intravenously as a 0.75 mg/kg bolus followed by continuous infusion of 1.75 mg/kg/hr during the procedure. ACT assays were performed immediately using a Hemochron 801 with FTCA510-4 ACT cartridges containing silica, phospholipids, and diatomaceous earth (kaolin). The open circle represents the mean (±SD) ACT and mean bivalirudin concentration at the 30 min time point in the 22 PCI patients.

The effects of PZ-128 micelles were measured on activated clotting time (ACT) in human blood samples freshly obtained from adult patients undergoing PCI. At concentrations of PZ-128 up to 150 µM, there were no effects on ACT in the human PCI blood samples (FIG. 5). By comparison, the ACT was highly elevated at the 30 min time period in all PCI patients who received intravenous infusions of the direct thrombin inhibitor, bivalirudin. Together, these data indicate that downstream inhibition of the platelet thrombin receptor with PZ-128 micelles does not adversely affect hemostasis or coagulation parameters in primates as compared to direct inhibition of thrombin.

Methods

Human Platelet Aggregation

Whole blood from healthy donors was collected into a 30 ml syringe containing sodium citrate (0.4% vol/vol final). Platelets were isolated from platelet rich plasma (PRP) using Sepharose 2B columns in modified PIPES buffer.

Human ACT Evaluation

Adult outpatients with angina referred for coronary angiography or PCI were enrolled in the Tufts Medical Center Adult Cardiac Catheterization Laboratory. Blood was collected prior to PCI or angiography and PZ-128 micelles were spiked into 1 ml samples of whole blood at a range of final concentrations (0-150 µmol/L). ACT was measured immediately in duplicate. To serve as a positive control for elevated ACT, blood was also collected from patients at the end of the PCI procedure, who received a weight-adjusted dosage of bivalirudin administered intravenously as a 0.75 mg/kg bolus followed by continuous infusion of 1.75 mg/kg/hr during the procedure. Bivalirudin concentrations in plasma were measured by LC/MS/MS.

Guinea Pig Arterial Thrombosis and Platelet Aggregation

Male Hartley guinea pigs (150~220 g) were purchased from Charles River Laboratories. A 0.61 mm-diameter catheter was inserted into the left jugular vein of anesthetized animals for administration of infusions of 5% USP dextrose vehicle or PZ-128 micelles. A 0.5 V-Doppler probe (Transonic Systems, Ithaca, N.Y.) was placed around the right carotid artery to record blood flow. A range of doses of PZ-128 micelles from 0.05 to 1.6 mg/kg in 0.9 ml volumes were delivered at an injection rate of 0.09 ml/min by a Harvard syringe pump. Five minutes after the infusion ended, arterial thrombosis was induced by placing a 5×5 mm$^2$ piece of filter paper soaked in freshly made 20% $FeCl_3$ solution on the right carotid artery 5 mm distal to the probe for 20 minutes. If vessel occlusion did not occur within 60 minutes of injury, the experiment was stopped and time to occlusion was assigned a value of 60 minutes. To examine possible synergistic effects of PZ-128 micelles and P2Y12-ADP receptor inhibition, 1 mg/kg clopidogrel was administered by oral gavage 4 hours prior to $FeCl_3$ injury. In these synergy experiments, the maximum endpoint was set at 90 minutes for occlusion time.

Guinea pigs weighing 600-650 g were used for platelet aggregation experiments. PZ-128 micelles (3 or 6 mg/kg) were administered by a 10 min intravenous infusion, and blood was collected by cardiac puncture into sodium citrate (0.4% vol/vol final) 5 minutes after cessation of the infusion. PRP was prepared and PPACK added to a final concentration of 100 µg/ml. PRP was calcified with 2.5 mM $CaCl_2$ and aggregation was performed as described above.

Baboon Arterial-Venous Shunt Thrombosis and Platelet Aggregation

Non-terminal thrombosis and platelet aggregation studies were performed on 12 healthy male baboons (*Papio anubis*) weighing 9-12 kg at the Oregon National Primate Research Center (ONPRC). Animals had a chronic exteriorized silicone rubber shunt (A-V shunt) placed between the femoral artery and vein, and arterial thrombosis on Dacron grafts (4 mm diameter) quantified. Whole blood (10 ml) was collected into PPACK at a final concentration of 100 µg/ml just prior to infusion (baseline) and 15 min to 24 h after the PZ-128 micelle infusion was terminated. Platelet counts and hematocrit were measured immediately. PRP was prepared from whole blood and platelet aggregation performed as described above. Bleeding time (BT) measurements were performed on the shaved volar surface of the forearm using the standard template method.

Quantification of PZ-128 in Baboon Plasma

Various doses of PZ-128 micelles were infused intravenously for 45 min to baboons. At sequential time points, whole blood was drawn into 3.2% citrate buffer and immediately centrifuged at 3000 rpm for 10 min. Platelet-poor plasma (PPP) samples were harvested and stored at −80° C. PZ-128 drug levels in PPP samples were determined was using an API 4000 LC/MS/MS system (Agilux Laboratories, Worcester, Mass.).

PT and aPTT Measurements in Cynomolgus Monkeys

PZ-128 micelles (0, 3, 10 or 30 mg/kg) were administered intravenously to 2.5-4.5 kg male and female cynomolgus monkeys by infusion over 1 h at MPI Laboratories (Mattawan, Mich.). Peripheral venous blood was collected from cynomolgus monkeys into $K_3$EDTA anticoagulant at baseline (Day −8) and at two time points (Day 1 and Day 5) after daily 1-h intravenous PZ-128 micelle infusions on days 1-4. PT and aPTT were analyzed immediately on a MLA-800 coagulation analyzer.

What I claim:

1. A pharmaceutical composition comprising micelles of palmitate-KKSRALF-NH$_2$ (palmitate-SEQ ID NO:2-NH$_2$) acid salts and an aqueous solution comprising dextrose at about 5% by weight.

2. The pharmaceutical composition of claim 1, wherein the palmitate-KKSRALF-NH$_2$ acid salts are in the form of acetic acid salts.

* * * * *

SEQUENCE LISTING

```
<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct

<400> SEQUENCE: 1

Ser Phe Leu Leu Arg Asn
1               5
```

```
<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Lys Lys Ser Arg Ala Leu Phe
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Arg Cys Leu Ser Ser Ser Ala Val Ala Asn Arg Ser
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Construct

<400> SEQUENCE: 4

Pro Ser Leu Ser Ser Ser Ala Val Ala Asn Arg Ser
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Asn Arg Ser Lys Lys Ser Ser Ala Leu Phe
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Construct

<400> SEQUENCE: 6

Ile Leu Lys Met Lys Val Lys Lys Pro Ala Val
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Thr Leu Gly Arg Ala Ser Phe
1               5

<210> SEQ ID NO 8
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Leu Ser Trp Arg Thr Leu Gly Arg Ala Ser Phe
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Synthetic Construct

<400> SEQUENCE: 9

Tyr Pro Met Gln Ser Leu Ser Trp Arg Thr Leu Gly Arg Ala Ser Phe
1               5                   10                  15

<210> SEQ ID NO 10
<211> LENGTH: 21
<212> TYPE: PRT
<213> ORGANISM: Artificial Sequence
<220> FEATURE:
<223> OTHER INFORMATION: Synthetic Construct

<400> SEQUENCE: 10

Phe Leu Ala Val Val Tyr Pro Met Gln Ser Leu Ser Trp Arg Thr Leu
1               5                   10                  15

Gly Arg Ala Ser Phe
            20

<210> SEQ ID NO 11
<211> LENGTH: 13
<212> TYPE: PRT
<213> ORGANISM: Artificial Sequence
<220> FEATURE:
<223> OTHER INFORMATION: Synthetic Construct

<400> SEQUENCE: 11

Ala Ser Ser Glu Ser Gln Arg Tyr Val Tyr Ser Ile Leu
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic Construct

<400> SEQUENCE: 12

Leu Ile Ser Tyr Val Tyr Arg Gln Ser Glu Ser Ser Ala
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct

<400> SEQUENCE: 13

Ala Tyr Pro Gly Lys Phe
1               5
```